(12) United States Patent
Burkholz et al.

(10) Patent No.: US 12,011,550 B2
(45) Date of Patent: Jun. 18, 2024

(54) CATHETER WITH AN ASYMMETRIC TIP (71) Applicant: Becton, Dickinson and Company, Franklin Lakes, NJ (US)

(72) Inventors: Jonathan Karl Burkholz, Salt Lake City, UT (US); Andrew Charles Farinella, Oradell, NJ (US); Daniel Kirk Hyer, Alpine, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/116,708

(22) Filed: Mar. 2, 2023

(65) Prior Publication Data

US 2023/0201527 A1 Jun. 29, 2023

Related U.S. Application Data

(60) Continuation of application No. 16/799,449, filed on Feb. 24, 2020, now Pat. No. 11,612,717, which is a division of application No. 15/286,261, filed on Oct. 5, 2016, now Pat. No. 10,610,668.

(51) Int. Cl.
*A61M 25/00* (2006.01)
*A61M 25/06* (2006.01)

(52) U.S. Cl.
CPC .... *A61M 25/0068* (2013.01); *A61M 25/0606* (2013.01); *A61M 25/007* (2013.01); *A61M 2025/0073* (2013.01); *A61M 25/0693* (2013.01)

(58) Field of Classification Search
CPC .......... A61M 25/0068; A61M 25/0023; A61M 25/007; A61M 25/0606
USPC ........................................................ 604/523
See application file for complete search history.

(56) References Cited

U.S. PATENT DOCUMENTS

| | | | |
|---|---|---|---|
| 4,583,968 A | 4/1986 | Mahurkar | |
| 4,588,398 A | 5/1986 | Daugherty et al. | |
| 5,352,205 A * | 10/1994 | Dales ................ | A61M 25/0637 604/165.03 |
| 2007/0088273 A1 | 4/2007 | Rafi | |
| 2009/0076435 A1 * | 3/2009 | Melsheimer ...... | A61M 25/0032 604/6.16 |

FOREIGN PATENT DOCUMENTS

| | | |
|---|---|---|
| JP | 2000319676 A | 11/2000 |
| JP | 2005532866 A | 11/2005 |
| JP | 2014525319 A | 9/2014 |

\* cited by examiner

*Primary Examiner* — Phillip A Gray
(74) *Attorney, Agent, or Firm* — Kirton McConkie; Whitney Blair; Kevin Stinger (57) ABSTRACT

A catheter may include a catheter body, which may include a proximal end, a distal end, and a lumen formed by an inner wall of the catheter body that extends between the proximal end and the distal end along a longitudinal axis. The distal end of the catheter body may include a distal lumen opening disposed on the longitudinal axis. The distal end may also include a leading edge. The leading edge may form the distal lumen opening and may include an upper and a lower portion. The lower portion of the leading edge may be disposed distally to the upper portion of the leading edge.

7 Claims, 10 Drawing Sheets

CATHETER WITH AN ASYMMETRIC TIP

RELATED APPLICATIONS

This application is a continuation of U.S. patent application Ser. No. 16/799,449, filed Feb. 24, 2020, entitled CATHETER WITH AN ASYMMETRIC TIP, which is a divisional of U.S. patent application Ser. No. 15/286,261, filed Oct. 5, 2016, entitled CATHETER WITH AN ASYMMETRIC TIP, which is incorporated herein in its entirety.

BACKGROUND OF THE INVENTION

The present invention relates generally to vascular access systems and components, including catheter assemblies and devices used with catheter assemblies. In particular, the present invention relates to systems and methods for improving a catheter tip to provide improved insertion, infusion flow rates, and fluid collection.

Vascular access devices are used for communicating fluid with the anatomy of a patient. For example, vascular access devices, such as catheters, are commonly used for blood sampling. Blood sampling is a common health care procedure involving the withdrawal of at least a sample of blood from a patient. Once collected, blood samples are analyzed via one or more blood test levels.

Vascular access devices are also commonly used for infusing fluid, such as saline solution, various medicaments, and/or total parenteral nutrition, into a patient, withdrawing blood from a patient, and/or monitoring various parameters of the patient's vascular system. A variety of clinical circumstances, including massive trauma, major surgical procedures, massive burns, and certain disease states, such as pancreatitis and diabetic ketoacidosis, can produce profound circulatory volume depletion. This depletion can be caused either from actual blood loss or from internal fluid imbalance. In these clinical settings, it is frequently necessary to infuse blood and/or other fluid rapidly into a patient to avert serious consequences.

In order to properly place a catheter vascular access device in a patient, the catheter is typically mounted over an introducer needle having a sharp distal tip. At least the distal portion of the catheter tightly engages the outer surface of the needle to prevent peel back of the catheter and thus facilitates insertion of the catheter into the blood vessel. The tip of the needle preferably extends beyond the tip of the catheter with the bevel of the needle facing up towards the patient's skin.

The catheter and needle are inserted at a shallow angle through the patient's skin into the blood vessel. In order to verify proper placement of the catheter and the needle in the blood vessel, the clinician may confirm that there is flashback of blood in a flashback chamber. The flashback chamber may typically be formed as part of the needle hub. Once proper placement of the catheter and needle assembly into the blood vessel is confirmed, the clinician applies pressure to the blood vessel by pressing down on the patient's skin over the blood vessel distal of the needle and the catheter. This finger pressure occludes or at least minimizes further blood flow through the needle and the catheter. The clinician then withdraws the needle, leaving the catheter n place for use in accordance with standard medical technique.

In some instances, an opening in a distal tip of the catheter may be at least partially obstructed or blocked by an inner wall of the blood vessel when the catheter is placed in the blood vessel. Obstruction of the opening in the tip of the catheter may restrict flow through the catheter, inhibiting fluid infusion and/or blood collection. In some instances, obstruction of the opening in the tip of the catheter and flow restriction through the catheter may also result in blood hemolysis, which may decrease a quality of a blood sample and may require additional samples to be taken.

BRIEF SUMMARY OF THE INVENTION

In some embodiments, the present invention is directed to a vascular access device that may provide for more efficient infusion and blood collection procedures, as well as collection of high quality blood samples. Thus, in some embodiments, the vascular access device may be configured to be used in combination with a vascular infusion system and/or a blood collection system. In some embodiments, the vascular access device may also provide improved insertion of a needle and catheter assembly. The vascular access device generally includes an intravenous catheter configured to access the vascular system of a patient.

In some embodiments, a catheter body of the intravenous catheter includes a proximal end, a distal end, and a lumen formed by an inner wall of the catheter body that extends between the proximal end and the distal end of the catheter body along a longitudinal axis. In some embodiments, the distal end may include a distal lumen opening disposed on the longitudinal axis. The term "leading edge" as used in the present disclosure may refer to an edge of the catheter body that forms the distal lumen opening and contacts the needle when the needle is in an insertion configuration. In some embodiments, the leading edge may include a distal-most surface of the catheter body. In some embodiments, the leading edge may include an upper portion and a lower portion. In some embodiments, the upper portion of the leading edge may be disposed closer to skin of a patient than the lower portion of the leading edge after the peripheral catheter is placed within a vein of the patient.

In some embodiments, the lower portion of the leading edge may be disposed distally to the upper portion of the leading edge. In these and other embodiments, the leading edge may be beveled between the upper portion and the lower portion of the leading edge. In some embodiments, an outer wall of the catheter body may include a tapered portion and an untapered portion. In some embodiments, the tapered portion may be disposed at least proximate the leading edge. In some embodiments, the tapered portion may taper inwardly at an angle between 2 and 30 degrees with respect to the longitudinal axis. In some embodiments, the tapered portion may be asymmetric. For example, a proximal end of a lower side of the tapered portion may be disposed distally to a proximal end of an upper side of the tapered portion. The term "symmetric" as used in the present disclosure may include symmetry about an axis or axisymmetry. The term "asymmetric" as used in the present disclosure may include asymmetry about an axis or non-axisymmetry.

In some embodiments, the tapered portion may include one or more flow holes. For example, an upper side of the tapered portion may include a single flow hole. In some embodiments, at least one third of a length of the upper side of the tapered portion may include the single hole.

In some embodiments, each of the flow holes may be in communication with the lumen and may include a passageway with an inner wall surface defining a first plane. In some embodiments, an orientation of the first plane to the longitudinal axis may be acute. For example, the orientation of the first plane to the longitudinal axis may be forty-five degrees.

In some embodiments, an inner wall of the catheter body may include a land portion at least proximate the leading edge. The land portion may be configured to contact the needle when the needle is inserted in the peripheral catheter. In some embodiments, one or more of the flow holes may include a passageway that extends through the land portion. In some embodiments, the land portion may be asymmetric. For example, a proximal end of one side of the land portion may be offset from a proximal end of an opposite side of the land portion, such that the two proximal ends are not diametrically opposed. In further detail, in some embodiments, the proximal end of the one side of the land portion may be distal to the proximal end of the opposite side of the land portion. In these and other embodiments, a cross-section of the land portion may be configured in a shape of a parallelogram.

In some embodiments, an inner wall of the catheter body may include a shoulder proximate to the land portion. In some embodiments, a portion of the inner wall corresponding to an upper edge of the shoulder may be angled with respect to the longitudinal axis and/or a portion of the inner wall corresponding to a lower edge of the shoulder may be angled with respect to the longitudinal axis. In some embodiments, the shoulder may be asymmetric. In some embodiments, the angle of the upper edge of the shoulder may be a same angle or a different angle as the angle of the lower edge of the shoulder.

In some embodiments, the distal end of the catheter body may include an external geometry defined by an outer wall of the distal end and an inner geometry defined by the inner wall of the distal end. In some embodiments, the distal end of the catheter body may be asymmetric. For example, the external geometry and/or the inner geometry of the catheter body may be asymmetric. Examples of an asymmetric distal end may include a distal end that includes one or more of the following: the lower portion of the leading edge disposed distally to the upper portion of the leading edge, a beveled leading edge between the upper and the lower portion of the leading edge, an asymmetric land portion, an asymmetric shoulder, an asymmetric tapered portion, etc. An asymmetric distal end may provide several advantages, as will be explained in further detail.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

As used herein, the term "proximal" may refer to a location with respect to the device that, after a catheter assembly is inserted into a patient during normal use, is closest to the clinician and farthest from the patient. Conversely, the term "distal" may refer to a location with respect to the device that, after the catheter assembly is inserted into the patient during normal use, is farthest from the clinician and closest to the patient. As used herein, the term "top," "up," "upper," or "upwardly" refers to a location with respect to the device that, after the catheter assembly is inserted into the patient during normal use, is radially away from the longitudinal axis of the device and toward the patients skin. Conversely, as used herein, the term "bottom," "lower," "down," or "downwardly" refers to a location with respect to the device that, after the catheter assembly is inserted into the patient during normal use, is radially away from the longitudinal axis of the device and away from the patient's skin.

Embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
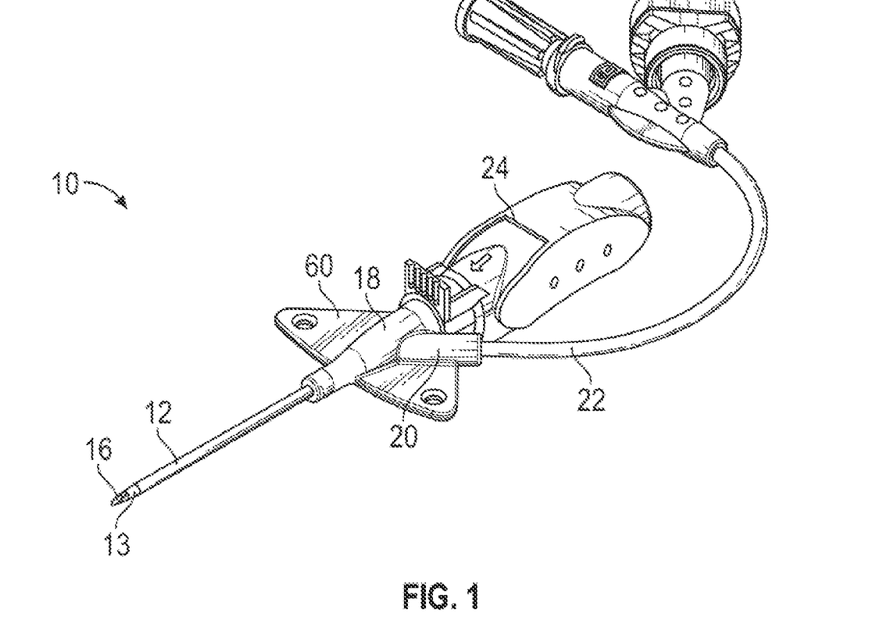
FIG. 1 is a perspective view of an example peripheral intravenous catheter, according to some embodiments.

Referring now to FIG. 1, a vascular access device may include a peripheral intravenous catheter 10 (referred to in the present disclosure as "PIVC 10"). Although this invention is described herein in connection with a PIVCC, it is to be understood that this invention is applicable to other catheters and vascular access devices. For some applications, the vascular access device is inserted into a peripheral vein of the patient. In other applications, the vascular access device is inserted into a central vein of the patient.

In some embodiments, the PIVC 10 may include a short or truncated catheter 12 (usually 13 mm to 52 mm) that is inserted into a small peripheral vein. For example, the PIVC 10 may include a diameter of approximately a 14 gauge catheter or smaller. However, the catheter 12 may be any length. There the length is selected based on the intended application of the catheter 12. The catheter 12 may also include any diameter, where the diameter is selected based on the intended application of the catheter 12.

In some embodiments, the introducer needle 16 may typically be inserted through the catheter 12 such that a sharp distal tip of the needle extends beyond a tip 13 of the catheter 12. Once the catheter 12 is inserted into the blood vessel 15 of the patient, the introducer needle 16 may be removed from an inner lumen of the catheter 12 to permit infusion and/or blood collection via the catheter 12.

Suitable materials for the catheter 1.2 may include, but are not limited to, thermoplastic resins such as fluorinated ethylene propylene (FEP), polytetrafluoroethylene (PTFE))), polyurethane, and the like. In some embodiments, the catheter 12 may be formed from a thermoplastic hydrophilic polyurethane that softens with exposure to physiological conditions present in the patient's body. The catheter 12 may include a flexible or semi-flexible biocompatible material, as commonly used in the art. In other embodiments, the catheter 12 may include a metallic material, such as surgical steel, titanium, cobalt steel, and the like. Additionally, in some embodiments, the material used to form the catheter 12 may be transparent or at least translucent. Additionally, in some embodiments, the catheter 12 may be formed so that it is partially transparent or translucent such as where catheter 12 is formed from stripes of transparent or translucent material. This may allow the clinician to see blood flashback in an annular space between the introducer needle 16 and the catheter 12 where the introducer needle 16 includes a notch, i.e. a hole or opening in the sidewalk adjacent to a distal end of the introducer needle 16 to allow such blood flow.

In some embodiments, the PIVC 10 may include a catheter adapter 18 that may house a proximal end of the catheter 12. Suitable materials for the catheter adapter 18 may include, but are not limited to, thermoplastic polymeric resins such as polycarbonate, polystyrene, polypropylene, poly ethylene phthalate glycol (PETG) and the like. In some embodiments, the material used to form the catheter adapter 18 may be transparent or at least translucent to allow the clinician to view blood flashback therein.

In some embodiments, the catheter adapter 18 may include a port 20 that is coupled with an extension tube 22. In some embodiments, the extension tube 22 may be coupled to upstream infusion and/or blood collection components. In some embodiments, the extension tube 22 may be translucent to allow the clinician to view flashback of blood therein to confirm successful venipuncture. In some embodiments, the extension tube 22 may be integrated with the catheter adapter 18, as described, for example, in further detail in U.S. Pat. No. 5,697,614.

In some embodiments, an inner lumen of the catheter adapter 18 may be in fluid communication with both an inner lumen of the extension tube 22 and the inner lumen of the catheter 12. In some embodiments, a tip of the introducer needle 16 may be defined by a bevel, and a proximal end of the introducer needle 16 may be connected to a needle hub 24. In some embodiments, the introducer needle 16 may be formed from stainless steel and may have a longitudinal axis that is generally parallel to a longitudinal axis of catheter 12 and/or the PIVC 10.

In some embodiments, the introducer needle 16 may be formed with a notch adjacent to the distal end of the introducer needle 16. This configuration may allow blood to flow into the open tip of the introducer needle 16 and then out of the notch into the annular space between the catheter 12 and the introducer needle 16. If the catheter 12 is at least translucent, the clinician may be able to observe blood flashback promptly upon successful venipuncture. Additionally, in some embodiments, when the blood flows into the extension tube 22, if extension tube 22 is at least translucent, the clinician may also be able to observe blood flashback in the extension tube 22. In some embodiments, where no notch is formed in the introducer needle 16, the needle hub 24 may include an integrated flashback chamber having an open proximal end that is closed to fluid flow by a vented plug that may allow air but not fluid to flow there through. The needle hub 24 may be formed from the same types of materials that are used to form the catheter adapter 18. Of course, other materials may be used to form the needle hub 24.

The catheter 12 of the PIVC 10 in accordance with the present invention may include a distal end or tip 13. The tip 13 may include an external geometry defined by an outer wall of the tip 13 and an inner geometry defined by an inner wall of the tip 13. In some embodiments, the tip 13 may be asymmetric. For example, the external geometry and/or the inner geometry of the tip 13 may be asymmetric. An asymmetric external geometry of the tip 13 and/or an asymmetric internal geometry of the tip 13 may provide several advantages, as will be explained in further detail.

Figure 2:
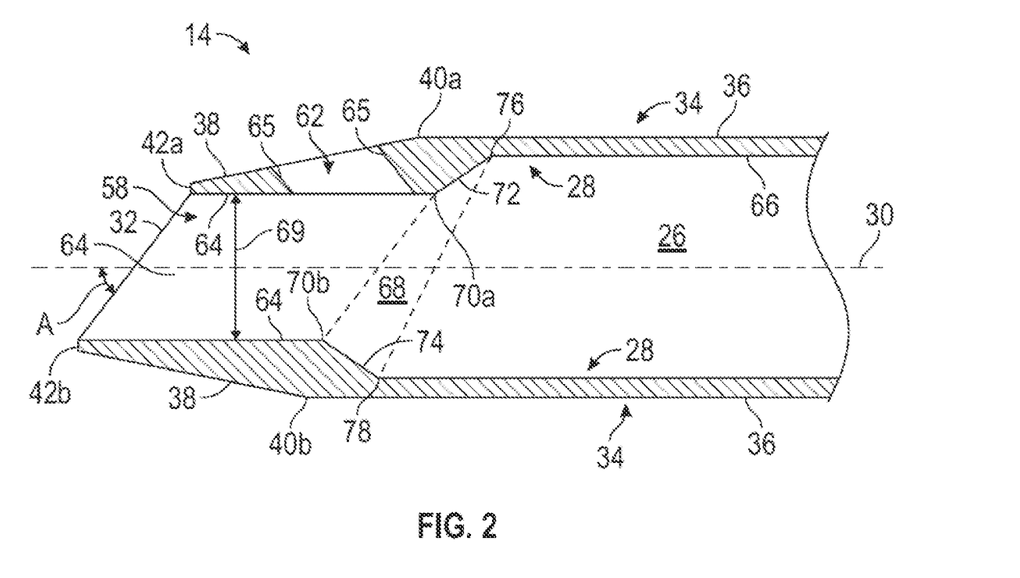
FIG. 2 is a longitudinal cross-sectional view of a portion of an example catheter that includes an asymmetric outer geometry and an asymmetric inner geometry, according to some embodiments.

Referring now to FIG. 2, a side view in cross section of the tip 14 of the catheter 12 is illustrated, according to some embodiments. In some embodiments, the tip 14 may correspond to the tip 13 of FIG. 1. In some embodiments, the tip 14 may include a central lumen 26 formed by the inner wall 28 of the tip 14. In some embodiments, the central lumen 26 may extend along a longitudinal axis 30 of the catheter 12 and may define a fluid flow path from a leading edge 32 of the tip 14 through to a proximal end of the catheter 12. In some embodiments, the leading edge 32 may include a width and a planar surface normal to the longitudinal axis 30 of the catheter 12, as illustrated in FIG. 2.

In some embodiments, the outer wall 34 may include an untapered portion 36 and/or a tapered portion 38. In some embodiments, the untapered portion 36 may be parallel to the longitudinal axis 30. In some embodiments, the tapered portion 38 may be proximal to the leading edge 32 and distal to the untapered portion 36. In some embodiments, the tapered portion 38 may taper inwardly at an angle of between about 10 and 45 degrees with respect to the longitudinal axis 30. In some embodiments, the tapered portion 38 may be terminated by the leading edge 32. In some embodiments, the tapered portion 38 may taper linearly inwardly towards the leading edge 32.

In some embodiments, the outer geometry of the tip 14 may be asymmetric, as illustrated in FIG. 2. For example, the proximal end 40a of one side of the tapered portion 38 may be offset from a proximal end 40b of an opposite side of the tapered portion 38, such that the two proximal ends 40a, 40b are not diametrically opposed. In some embodiments, the proximal end 40b, which may be disposed on a lower side of the tapered portion 38, may be disposed distally to the proximal end 40a, which may be disposed on an upper side of the tapered portion 38.

Additionally or alternatively, in some embodiments, upper and lower portions 42a, 42b of the leading edge 32, disposed on opposite sides of the tip 14, may be offset such that the upper and the lower portions 42a, 42b are not diametrically opposed, and the leading edge 32 is beveled. In some embodiments, the upper portion 42a may include an upper-most portion of the leading edge 32, and the lower portion 42b may include a lowest portion of the leading edge 32. In some embodiments, the lower portion 42b of the leading edge 32 may be disposed distally to the upper portion 42a of the leading edge 32. The leading edge 32 may be beveled between the upper and lower portions 42a, 42b at various angles, such as for example, between 20 and 80 degrees with respect to the longitudinal axis 30. This angle is shown at "A" on FIG. 2.

The asymmetric outer geometry of the tip 14 may improve insertion performance of the catheter 12. For example, in some embodiments, the asymmetric outer geometry may provide a smooth and more gradual transition from a smaller profile of the introducer needle 16 to a larger profile of the tip 14 outer diameter. The asymmetric outer geometry of the tip 14 may also reduce a penetration force necessary to penetrate the skin and/or the blood vessel 15 of the patient with the vascular access device. In some embodiments, the asymmetric outer geometry may reduce a force spike felt by the clinician as the tip 14 is inserted in the skin and/or the blood vessel 15 of the patient, providing a smoother insertion experience. Further, in some embodiments, because the leading edge 32 is beveled between the upper and lower portions 42a, 42b and the tip of the introducer needle 16 is also beveled, the tip 14 may be easily fit or be inserted into a shape of an opening in the blood vessel 15 of the patient created by the tip of the introducer needle 16 when the introducer needle 16 and the catheter 12 are placed in the blood vessel 15 of the patient, also providing a smoother insertion experience. A particular asymmetric outer geometry that includes leading edge 32 that is beveled between the upper portion 42a and the lower portion 42b may facilitate threading or advancing of the catheter 12 while retracting the introducer needle 16.

Figure 3A:
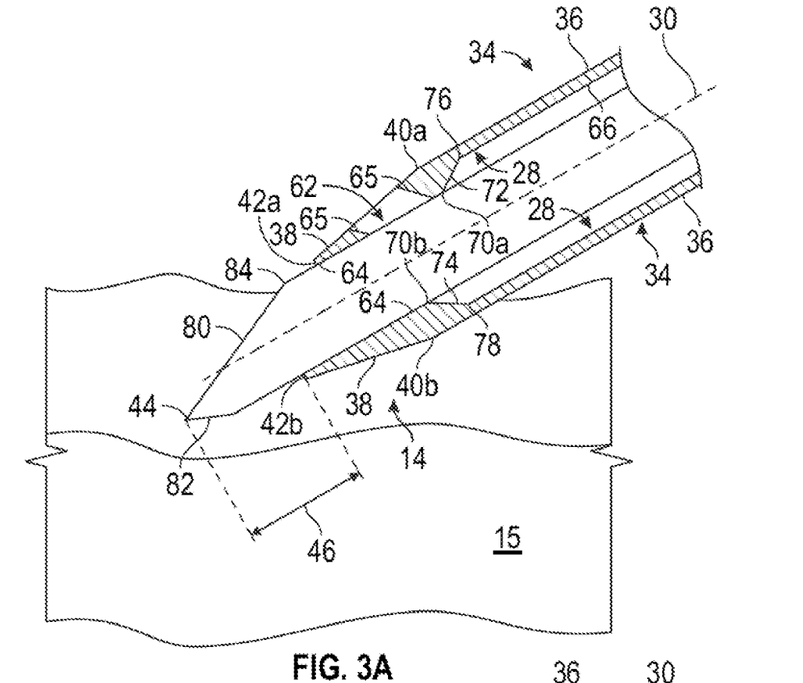
FIG. 3A is a longitudinal cross-sectional view of the portion of the catheter of FIG. 2 coupled with an example introducer needle in an insertion configuration, according to some embodiments.

Referring now to FIG. 3A, in some embodiments, the introducer needle 16 may include a primary bevel 80 and/or a secondary bevel 82. In some embodiments, when the vascular access device is in an insertion configuration for insertion of the introducer needle 16 and catheter 12 into the vein of the patient, the lower portion 42b of the leading edge 32 may be disposed distal to a primary bevel heel 84, which may facilitate introduction of the tip 14 into an incision made by the introducer needle 16 prior to insertion of a full diameter of the needle 16 into the incision. In these embodiments, in response to the introducer needle 16 being inserted into the incision past the secondary bevel 82, no additional cutting of the skin may occur as the needle 16 and the tip 14 are inserted into the vein of the patient. Instead, the skin may stretch over the tip 14 and/or the introducer needle 16 as a circumference of a widthwise cross-section of the needle 16 disposed in the incision increases and the primary bevel 80 fully penetrates the incision. In some embodiments, the lower portion 42b of the leading edge 32 may be disposed between the primary bevel heel 84 and the secondary bevel 82 in the insertion configuration, which may allow a portion of the tip 14 to be inserted into the incision without stretching the skin to a full or greatest outer diameter of the introducer needle 16.

Figure 3B:
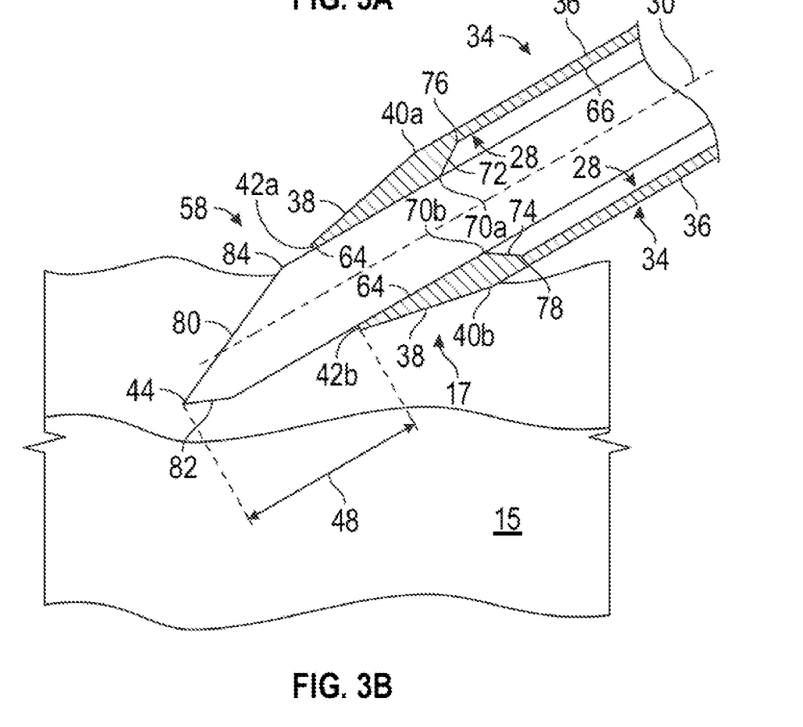
FIG. 3B is a longitudinal cross-sectional view of a portion of another example catheter with a symmetric outer geometry and a symmetric inner geometry, coupled with the introducer needle in the insertion configuration, according to some embodiments.

The asymmetric outer geometry may also improve insertion performance by reducing a lie distance, or a distance between the tip of the introducer needle 16 and the lower portion 42b of the leading edge 32, during insertion. For example, when the tip 44 of the introducer needle 16 is exposed from the tip 14 having the asymmetric outer geometry, the lie distance may equal a first distance 46. As illustrated in FIG. 3B, when the tip 44 of the introducer needle 16 is exposed from a tip 17 having a symmetric outer geometry, the lie distance may equal a second distance 48. The first distance 46 may be less than the second distance 48. A reduced lie distance may improve a likelihood that the tip 14 is within the blood vessel 15 upon initial blood flashback and/or may reduce a risk of damaging or transfixing the blood vessel 15 during insertion of the introducer needle 16 and the tip 14 into the blood vessel 15.

These and other benefits of the asymmetric outer geometry may be realized when the tip 14 of the catheter 12 is inserted at a shallow angle through the patient's skin into the blood vessel 15 of the patient. In further detail, after the catheter 12 is placed at a shallow angle into the blood vessel 15, a position of the tip 14 of the catheter 12 relative to the blood vessel 15 may impact a fluid flow rate that can be provided during infusion therapy and/or blood collection. A distal lumen opening may be formed by a leading edge of the tip 14, such as, for example, the leading edge 32. Referring back to FIG. 1, because many of the benefits of the asymmetric outer geometry may be realized when the tip 13 of the catheter 12 is inserted at the shallow angle into the blood vessel 15 of the patient, the PIVC 10 may include wings 60 or a securement platform, which may aid a clinician in precisely manipulating and controlling a position of the catheter 12 during venipuncture.

In some embodiments, the catheter 12 may include one or more flow holes 62, each of which may extend through the outer wall 34 and the inner wall 28 at a predetermined bore angle. In some embodiments, one or more of the flow holes 62 may be disposed in an upper side of the tapered portion 38, which may reduce direct impingement of infusates on the venous wall and/or allow increased flow into the one or more flow holes 62 during blood draw. The flow holes 62 may each include a passageway that includes an inner wall surface 65 defining a first plane. In some embodiments, an orientation of the first plane to the longitudinal axis 30 may be acute. For example, the orientation of the first plane to the longitudinal axis 30 may between about fifteen degrees and seventy-five degrees. In some embodiments, the orientation of the first plane to the longitudinal axis 30 may be about forty-five degrees. In some embodiments, the bore angle of a particular flow hole 62 may be selected so as to optimize flow efficiency through the particular flow hole 62 and/or provide a flow path redundancy, reducing catheter tension within the vein, system pressure, and tip jet velocity.

In some embodiments, the flow holes 62 may generally be provided to divert fluid from the main channel of flow through the central lumen 26 of the catheter 12. As such, the flow holes 62 may effectually slow the jet of infusant which issues from the tip 14 during infusion procedures. In some embodiments, the flow holes 62 may reduce exit velocity of an infusant during infusion procedures, including rapid infusion procedures. Additionally, the flow holes 62 may create a flow path redundancy to relieve the overall pressure in the tip 14.

In these and other embodiments, the upper side of the tapered portion 38 may include a single flow hole 62. In some embodiments, a large single flow hole 62, as opposed to multiple smaller flow holes 62, may reduce a risk of blood clot formation and eventual occlusion of the single flow hole 62. In some embodiments, at least one third of a length of the upper side of the tapered portion 38 may include the single flow hole 62.

One having skill in the art will appreciate that the number and dimensions of the flow holes 62 may be varied and adjusted to achieve a desired flow rate, a reduction in tip jet velocity, a reduction in vascular damage, and/or increased bolus density. The one or more flow holes 62 may generally be provided by manufacturing methods known in the art. For example, in some embodiments the one or more flow holes 62 may be provided with a laser drill.

Figure 4A:
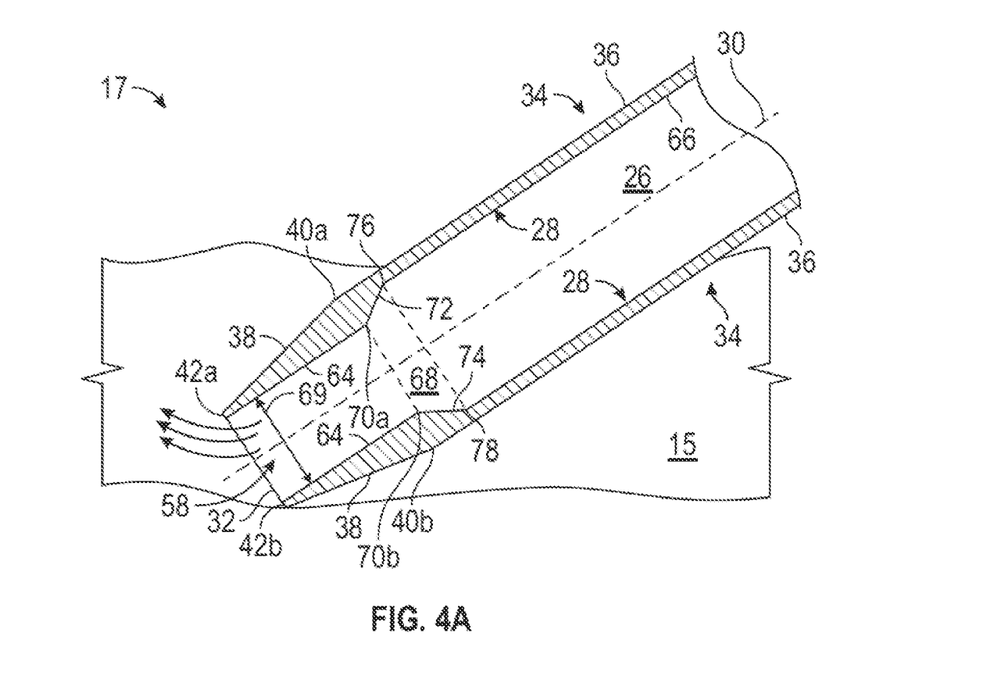
FIG. 4A is a longitudinal cross-sectional view of the catheter of FIG. 3B being used for infusing a fluid into a patient, according to some embodiments.
Figure 4B:
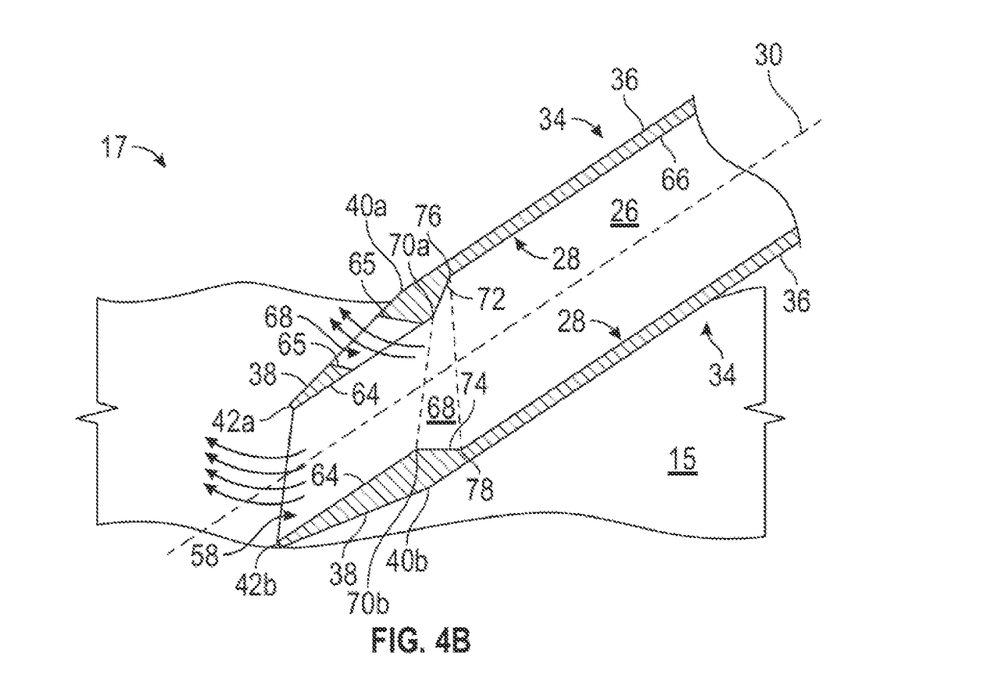
FIG. 4B is a longitudinal cross-sectional view of the catheter of FIG. 2 being used for infusing a fluid into a patient, according to some embodiments.

Referring now to FIG. 4A, in some instances, when the tip 17 with a symmetric outer geometry is inserted in the blood vessel 15 of the patient at the shallow angle, the distal lumen opening 58 of the catheter 12 may be partially obstructed or blocked by the inner wall of the blood vessel 15 due to an angle of the distal lumen opening 58 with respect to the inner wall of the blood vessel 15. For example, as illustrated in FIG. 4A, the angle of the distal lumen opening 58 of a particular catheter 12 with a symmetric outer geometry may be less than ninety degrees with respect to the blood vessel 15, inhibiting flow through the distal lumen opening 58. In contrast, referring now to FIG. 4B, the asymmetric outer geometry of the tip 14 may reduce obstruction or blocking of the distal lumen opening 58 of the catheter 12, which may be oriented perpendicularly with respect to the inner wall of the blood vessel 15 when the tip 14 is inserted in the blood vessel 15. As also illustrated in FIGS. 4A-4B, in some embodiments, the asymmetric outer geometry may increase a cross sectional area of the distal lumen opening 58 of the catheter 12 and allow an increased flow rate through the distal lumen opening 58. As illustrated in FIGS. 4A-4B, in some embodiments, the asymmetric outer geometry of the tip 14 may direct infusate towards a center of the blood vessel 15 compared to the symmetric outer geometry of the tip 17.

Figure 5A:
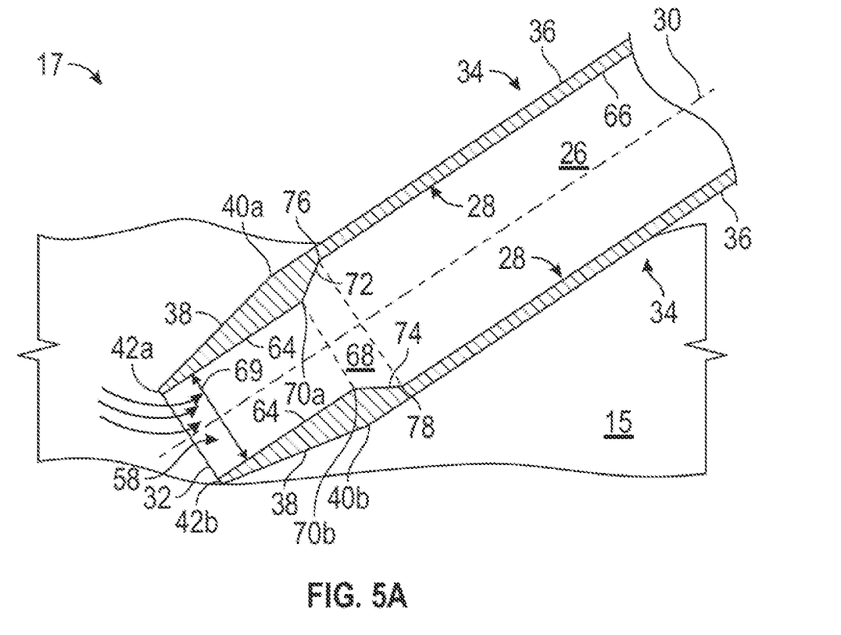
FIG. 5A is a longitudinal cross-sectional view of the catheter of FIG. 3B being used for blood collection from the patient, according to some embodiments.
Figure 5B:
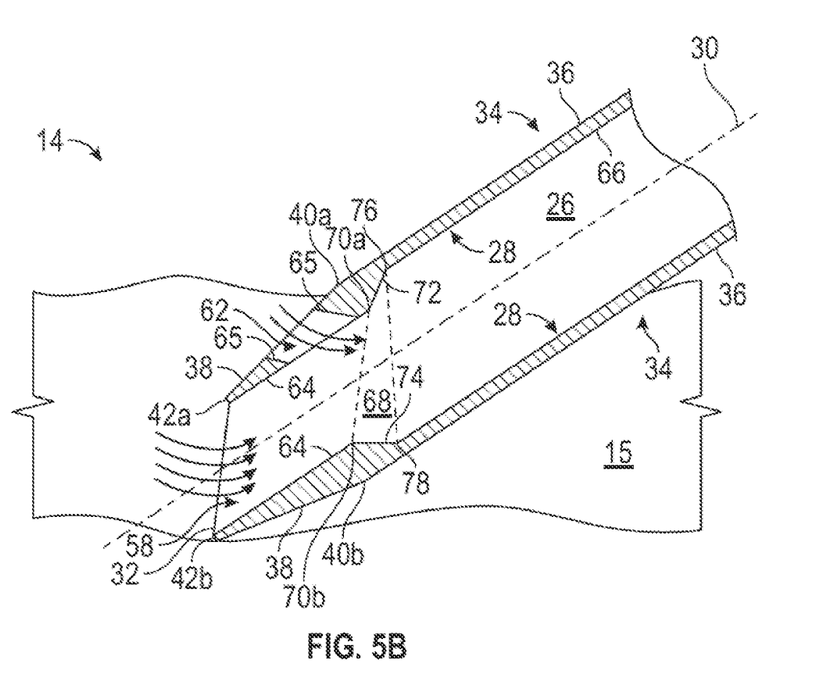
FIG. 5B is a longitudinal cross-sectional view of the catheter of FIG. 2 being used for blood collection from the patient, according to some embodiments.

Flow restriction, which may result from, for example, kinking, blockage of a particular catheter against the blood vessel 15, clotting, and/or other indwelling factors, may affect an ability of the clinician to obtain a sufficient amount of blood from the patient through the particular catheter. Flow restriction may also result in hemolysis, impacting a quality of a blood sample. Referring now to FIGS. 5A-5B, the asymmetric outer geometry of the tip 14 may improve line draw success and/or reduce hemolysis of blood samples collected using the tip 14 as compared to the tip 17.

For example, as illustrated in FIGS. 5A-5B, the asymmetric outer geometry of the tip 14 may reduce obstruction or blocking of the distal lumen opening 58 of the catheter 12 by the blood vessel 15 and/or increase the cross sectional area of the distal lumen opening 58, lowering localized pressure at the tip 14 during blood collection. Furthermore, the flow holes 62 may provide a flow path redundancy and/or may allow blood to be collected more rapidly. As mentioned, in some embodiments, a large single flow hole 62, as opposed to multiple smaller flow holes 62, may reduce a risk of blood clot formation and eventual occlusion of the single flow hole 62. The asymmetric outer geometry of the tip 14, as compared with the symmetric outer geometry of the tip 17, may place the distal lumen opening 58 into a position and angle similar to a needle-based blood draw system and position the distal lumen opening 58 further away from the wall of the blood vessel 15.

In some embodiments, the tip 17 may exhibit catheter penetration force peaks of similar or greater magnitude as compared with cannula penetration force peaks, while the asymmetric outer geometry of the tip 14 may provide spatial and temporal distribution of contact between the leading edge 32 of the tip 14 and the skin and/or blood vessel 15 of the patient, which may lower a magnitude and broaden a width of the catheter penetration force peak. In some embodiments, the tapering of the upper portion and/or the lower portion 42b (illustrated in FIG. 10) may reduce the penetration force by reducing surface area of the tip 14 normal to the skin and/or the blood vessel 15.

Referring back to FIG. 2, in some embodiments, the catheter 12 may have an internal geometry defined by the inner wall 28. For example, the inner wall 28 may include a distal land portion 64, a proximal portion 66, and a shoulder 68 connecting the land portion 64 and the proximal portion 66. A diameter 69 of the land portion 64 may be slightly less than a diameter of the introducer needle 16 near the tip 44 of the introducer needle 16 such that there is a friction fit between the land portion 64 and the introducer needle 16. Thus, in some embodiments, the land portion 64 of the tip 14 may conform tightly to the outer surface of the introducer needle 16.

In some embodiments, the land portion 64 may extend from the leading edge 32 to the shoulder 68. In some embodiments, the land portion 64 may be asymmetric. For example, a proximal end 70a of one side of the land portion 64 may be offset from a proximal end 70b of an opposite side of the land portion 64, such that the two proximal ends 70a, 70b are not diametrically opposed. In some embodiments, a cross-section of the land portion 64 may have a shape of a parallelogram, as illustrated in FIG. 2. In some embodiments, the proximal end 70b, which may be disposed on a lower side of the land portion 64, may be disposed distally to the proximal end 70a, which may be disposed on an upper side of the land portion 64. In some embodiments, the land portion 64 may be terminated by the leading edge 32.

In some embodiments, a portion of the inner wall 28 corresponding to an upper edge 72 of the shoulder 68 may be disposed at an angle with respect to the longitudinal axis 30. Additionally or alternatively, in some embodiments, a portion of the inner wall 28 correspond to a lower edge 74 of the shoulder 68 may be disposed at an angle with respect to the longitudinal axis 30. For example, the upper edge 72 may be disposed at an angle of between about 10 degrees and 80 degrees with respect to the longitudinal axis 30. For example, the lower edge 74 may be disposed at an angle of between about 10 degrees and 80 degrees with respect to the longitudinal axis 30. In some embodiments, the upper edge 72 may be more angled than the lower edge 74 with respect to the longitudinal axis 30. In some embodiments, a cross-section of the shoulder 68 may have a shape of a quadrilateral.

In some embodiments, the shoulder 68 may be asymmetric. For example, a proximal end 76 of the upper edge 72 may be offset from a proximal end 78 of the lower edge 74, such that the proximal end 76 of the upper edge 72 and the proximal end 78 of the lower edge 74 are not diametrically opposed. In these embodiments, a straight line segment extending from the proximal end 76 of the upper edge 72 to a proximal end 78 of the lower edge 74 may not be normal to the longitudinal axis of the catheter 12. Additionally or alternatively, in some embodiments, a distal end of the upper edge 72, which may correspond to the proximal end 70a of the land portion 64, may be offset from a distal end of the lower edge 74, which may correspond to the proximal end 70b of the land portion 64, such that the distal end of the upper edge 72 and the distal end of the lower edge 74 are not diametrically opposed.

The tip 14 having an asymmetric shoulder 68 and/or an asymmetric land portion 64 may affect flow dynamics within the tip 14 by, for example, directing flow through the flow hole 62 illustrated in FIG. 2 and/or other flow holes 62.

In some embodiments, the passageway of each of the one or more of the flow holes 62 may extend through the land portion 64. In some embodiments, the passageway of one or more flow holes 62 may extend through an upper side of the land portion 64 and/or an upper side of the tapered portion 38. In some embodiments, the one or more flow holes 62 may be disposed in the land portion 64 to prevent blood from exiting the one or more flow holes 62 during insertion. In further detail, in some embodiments, the notch adjacent to the tip 44 or distal end of the introducer needle 16 may be disposed proximal to a portion of the introducer needle 16 that contacts the land portion when the introducer needle 16 and the catheter 12 are inserted into the blood vessel 15 of the patient.

Figure 6:
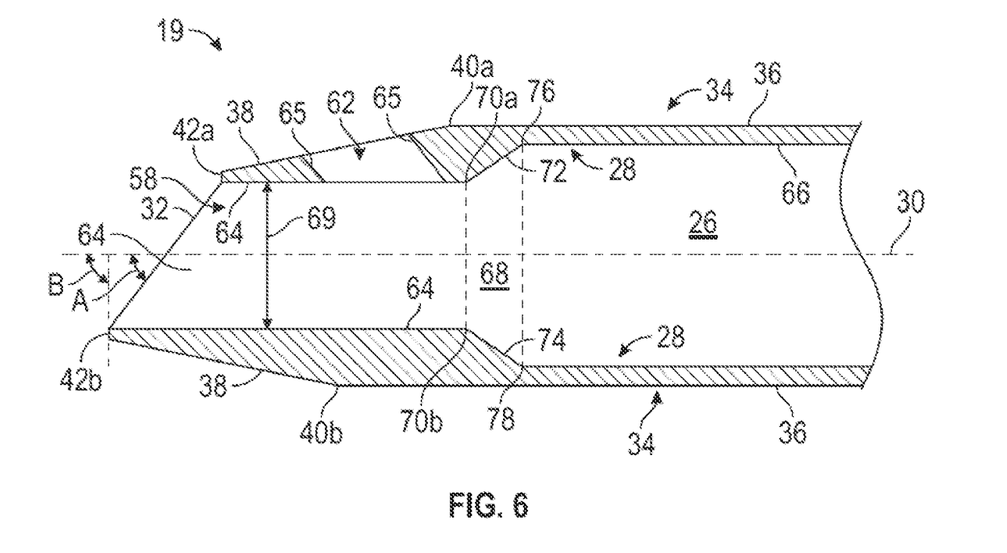
FIG. 6 is longitudinal cross-sectional view of a portion of another example catheter that includes an asymmetric outer geometry and a symmetric inner geometry, according to some embodiments.

Referring now to FIG. 6, in some embodiments, a tip 19 may have an asymmetric outer geometry formed by the outer wall 34 and a symmetric inner geometry formed by the inner wall 28. For example, the proximal end 70a of one side of the land portion 64 may be aligned with the proximal end 70b of an opposite side of the land portion 64, such that the two proximal ends 70a, 70b are diametrically opposed, as illustrated in FIG. 6. In these embodiments, a straight line segment extending from the proximal end 76 of the upper edge 72 to a proximal end 78 of the lower edge 74 may be normal to the longitudinal axis of the catheter 12. In some embodiments, the tip 19 may correspond to the tip 13 of FIG. 1 or the tip 14 of FIG. 2. In some embodiments, the proximal end 70b, which may be disposed on a lower side of the land portion 64, may be disposed distally to the proximal end 70a, which may be disposed on an upper side of the land portion 64. In some embodiments, the inner geometry of the tip 14 may be symmetric except for presence of the one or more flow holes 62 disposed in the upper side of the tapered portion 38, which may be absent from the lower side of the tapered portion 38. In some embodiments, the one or more flow holes 62 may be disposed in the upper side of the tapered portion 38 and/or the lower side of the tapered portion 38.

Figure 7:
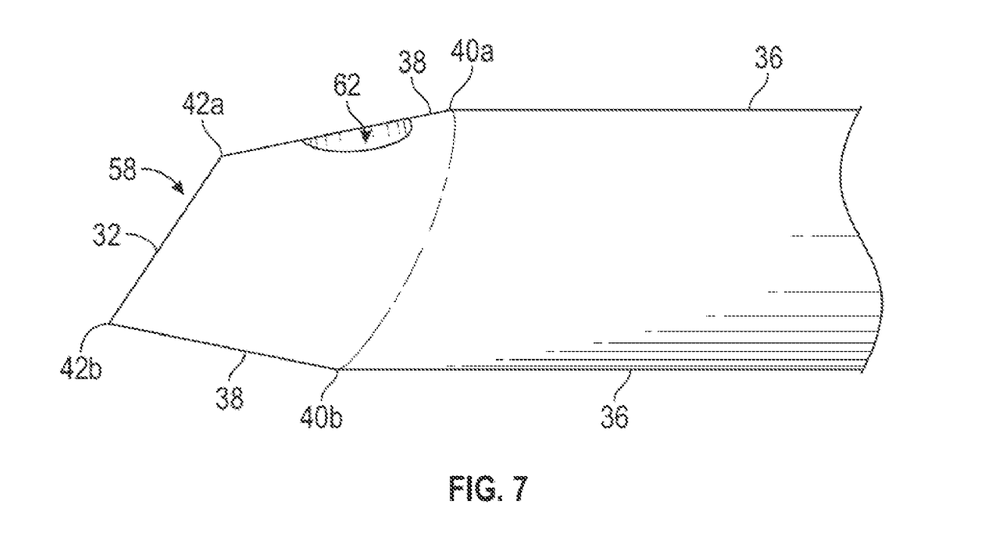
FIG. 7 is a side view of the catheter of FIG. 2 or 6, according to some embodiments.
Figure 8:
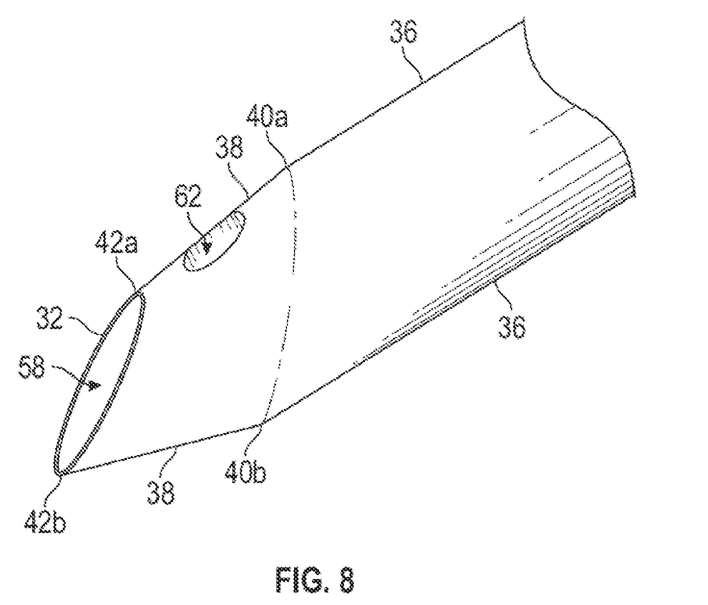
FIG. 8 is an upper perspective view of the catheter of FIG. 2 or 6, according to some embodiments.

FIGS. 7-8 are now referred to, which illustrate a circular flow hole 62. However, in some embodiments, one or more of the flow holes 62 may be non-circular. A circular flow hole 62 may issue a substantially cylindrical jet of fluid into the vasculature of a patient. In general, the substantially cylindrical jet may be concentrated and direct and break up slowly within the vein. It follows that a non-circular flow hole 62 (not illustrated) may issue a jet of fluid having a substantially non-circular cross section, and thus greater surface area. The increase in surface area of the jet issuing from the non-circular flow hole 62 may increase a rate of momentum transfer between the jet and the intravenous environment compared to that of more cylindrical jet of FIG. 7. Thus, the jet issuing from the non-circular flow hole 62 may disperse and decelerate more quickly, posing less of a threat of extravasation to vein walls.

Referring now to FIG. 8, in some embodiments, the leading edge 32 of a particular catheter tip with an asymmetric outer geometry, such as, for example, the tip 14 of FIG. 2 or the tip 19 of FIG. 6, may form a circle, an ellipse, or another shape. In some embodiments, a line segment extending from the upper portion 42a to the lower portion 42b of the leading edge 32 may not be normal to the longitudinal axis of the catheter 12 and/or the needle 16. As illustrated in FIG. 8, in some embodiments, the leading edge 32 of the particular catheter tip may form an ellipse. In contrast, the leading edge 32 of the tip 17, which may include a symmetric outer geometry as illustrated, for example, in FIG. 4A, may form a circle, which may lie in a plane normal to the longitudinal axis of the catheter 12.

Figure 9:
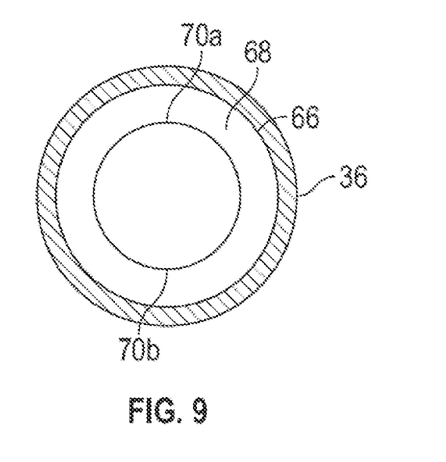
FIG. 9 is a cross-sectional view of the catheter of FIG. 2 or 6, according to some embodiments.

Referring now to FIG. 9, in some embodiments, the shoulder 68 may be asymmetric and annular. A particular shoulder 68 that is symmetric may also be annular.

Figure 10:
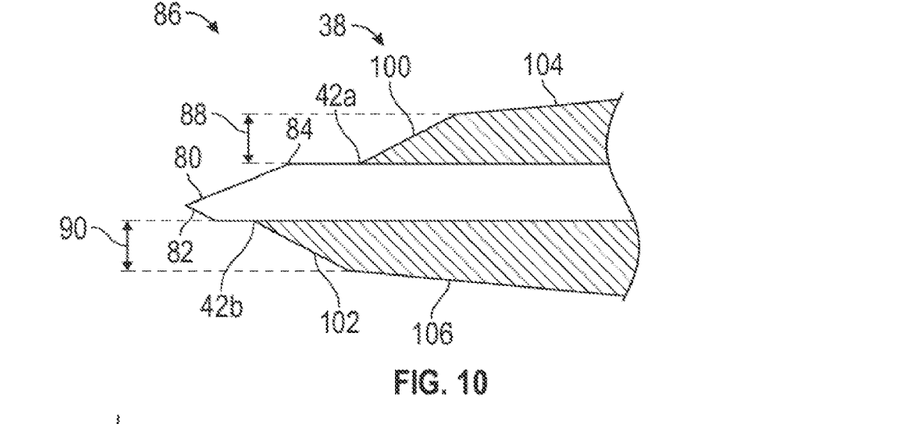
FIG. 10 is a cross-sectional view of a portion of another example catheter, according to some embodiments.

Referring now to FIG. 10, in some embodiments, the tip 86 may correspond to the tip 13, the tip 14, or the tip 19 of the previous Figures. In some embodiments, the outer geometry of the tip 86 may facilitate introduction of the catheter 12 into the incision made by the needle 16. In further detail, in some embodiments, a first upper portion 100 of the tapered portion 38 and/or a first lower portion 102 of the tapered portion 38 may be tapered at an angle between 10 and 45 degrees with respect to the longitudinal axis of the catheter 12. In some embodiments, the first upper portion 100 and/or the first lower portion 102 may be tapered with respect to the longitudinal axis of the catheter 12 at same or different angles from each other.

In some embodiments, a second upper portion 104 of the tapered portion 38 and/or a second lower portion 106 of the tapered portion 38 may be tapered at an angle between 2 and 30 degrees with respect to the longitudinal axis of the catheter 12. In some embodiments, the second upper portion 104 and/or the second lower portion 106 may be tapered with respect to the longitudinal axis of the catheter 12 at same or different angles from each other.

In some embodiments, a radial height of the tapered portion 38 may be uniform or variable around a particular circumference of the tapered portion 38. In some embodiments, a radial height 88 of the first upper portion 100 and/or a radial height 90 of the first lower portion 102 may be between 0.0005 and 0.003 inches. In some embodiments, the radial height 88 of the first upper portion 100 may be different from the radial height 90 of the first lower portion 102. In some embodiments, the radial height 88 of the first upper portion 100 may be the same as the radial height 90 of the first lower portion 102.

In some embodiments, the first upper portion 100 may be tapered at an angle greater than the second upper portion 104 with respect to the longitudinal axis of the catheter 12, which may facilitate introduction of the catheter 12 into the incision made by the needle 16. Additionally or alternatively, in some embodiments, the first lower portion 102 may be tapered at an angle greater than the second lower portion 106, which may facilitate introduction of the catheter 12 into the incision made by the needle 16.

Figure 11A:
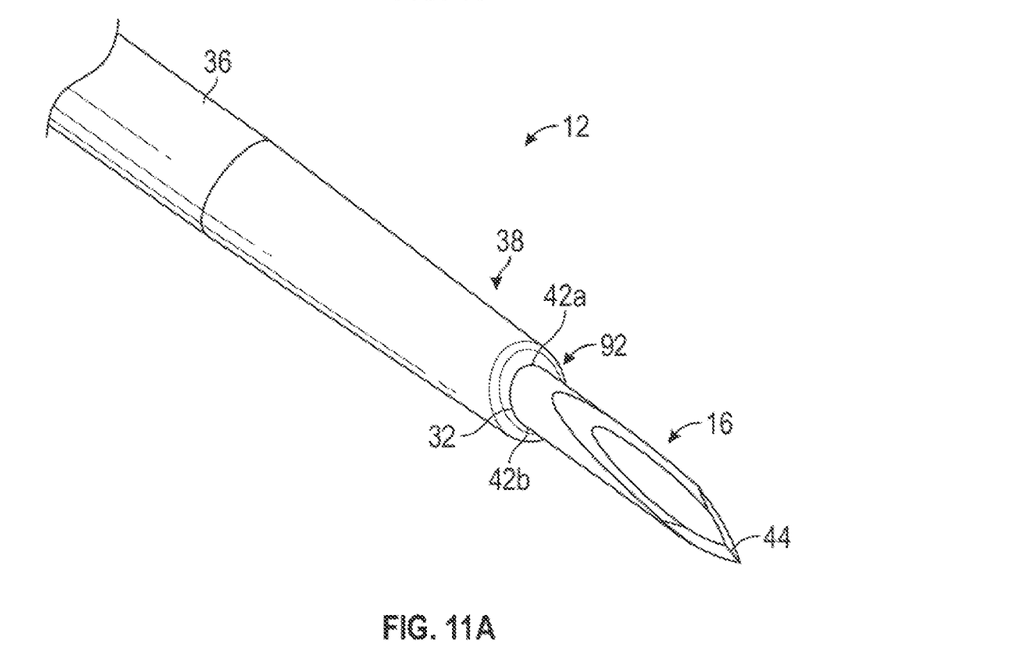
FIG. 11A is an upper perspective view of a portion of another example catheter coupled with an example introducer needle, according to some embodiments.
Figure 11B:
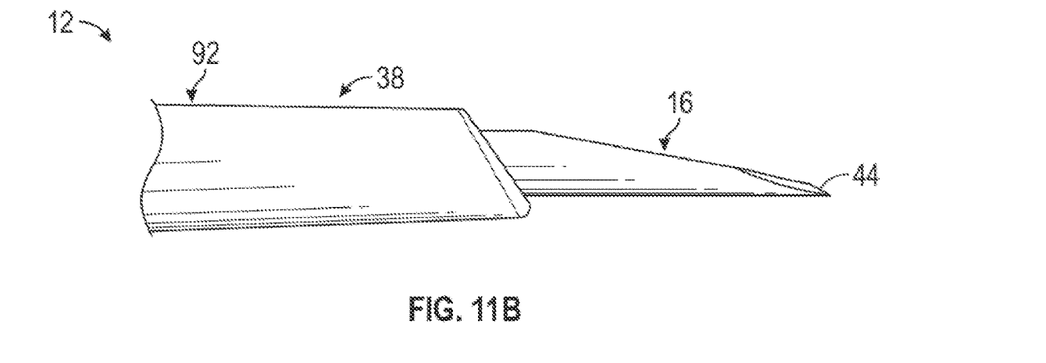
FIG. 11B is a side view of another portion of the catheter of FIG. 11A coupled with the introducer needle, according to some embodiments.
Figure 12A:
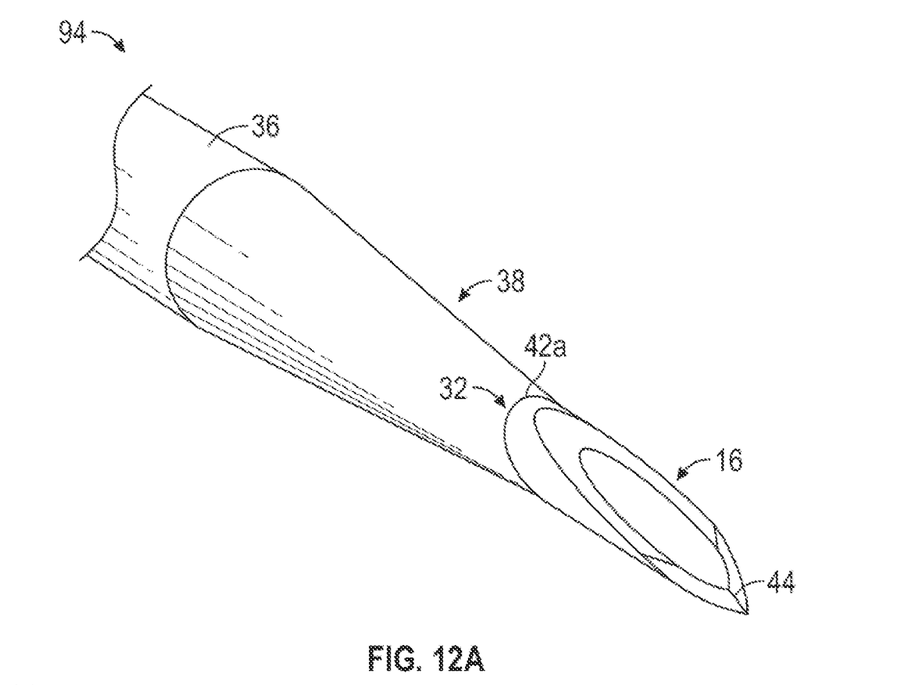
FIG. 12A is an upper perspective view of a portion of another example catheter coupled with an example introducer needle, according to some embodiments.
Figure 12B:
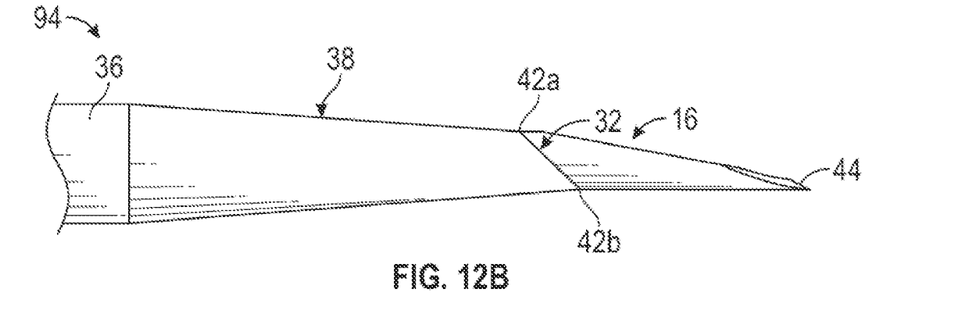
FIG. 12B is a side view of the portion of the catheter of FIG. 12A coupled with the introducer needle, according to some embodiments.
Figure 12C:
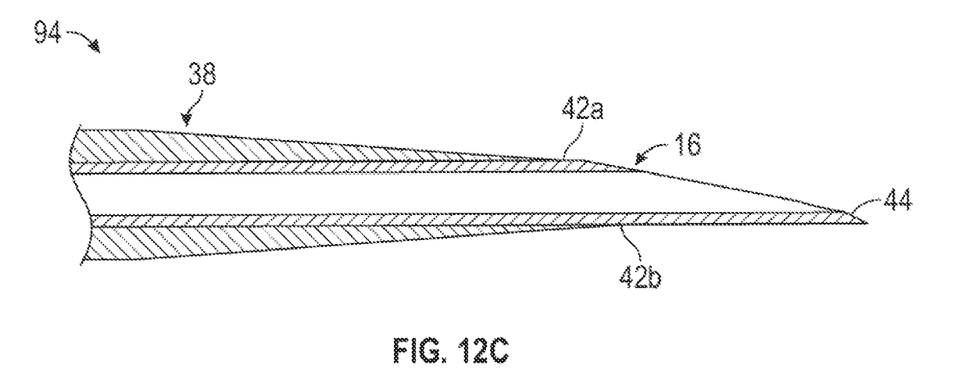
FIG. 12C is a cross-sectional view of the portion of the catheter of FIG. 12A coupled with the introducer needle, according to some embodiments.

Referring now to FIGS. 11A-11B, in some embodiments, the tapered portion 38 of a catheter tip 92 of the catheter 12 may be non-linearly tapered or curved. In some embodiments, the tip 92 may correspond to the tip 13, the tip 14, or the tip 19 of the previous Figures. Referring now to FIGS. 12A-12C, in some embodiments, a radius of the tapered portion 38 may decrease linearly along an entire length of the tapered portion 38 to the leading edge 32. In some embodiments, the leading edge 32 may be planar.

Figure 13A:
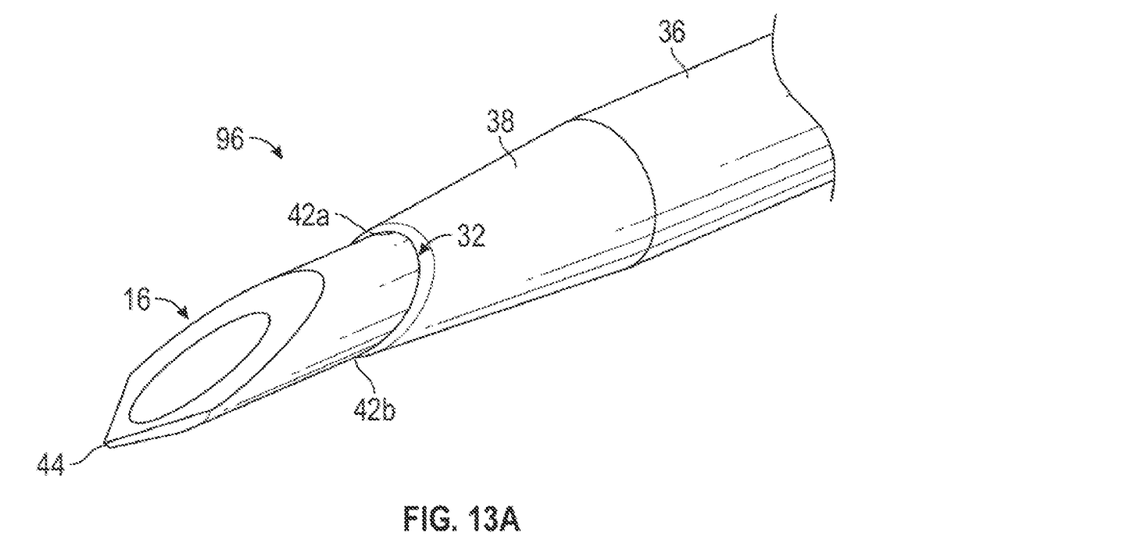
FIG. 13A is an upper perspective view of a portion of another example catheter coupled with an example introducer needle, according to some embodiments.
Figure 13B:
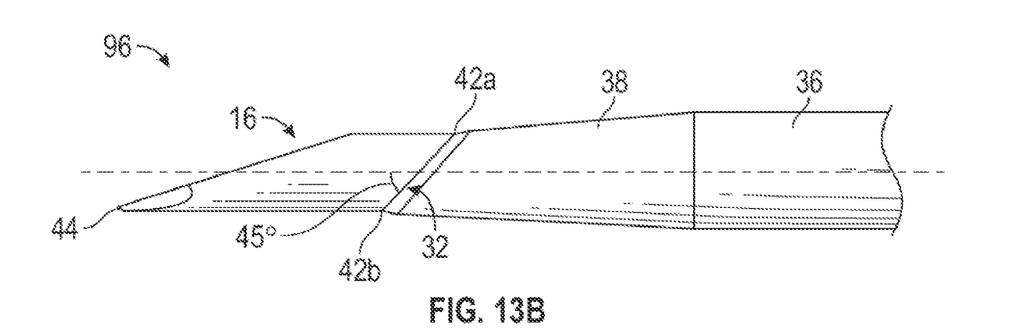
FIG. 13B is a side view of the portion of the catheter of FIG. 13A coupled with the introducer needle, according to some embodiments.

Referring now to FIGS. 13A-13B, in some embodiments, the leading edge 32 of a catheter tip 96 of the catheter 12 may be beveled between the upper and lower portions 42a, 42b at an angle. In some embodiments, the leading edge 32 may be beveled between the upper and lower portions 42a, 42b at an angle between 30 and 80 degrees with respect to the longitudinal axis of the catheter 12. As illustrated in FIGS. 13A-13B, in some embodiments, the leading edge may be beveled between the upper and lower portions 42a, 42b at an angle of 45 degrees with respect to the longitudinal axis of the catheter 12. In some embodiments, the ellipse formed by the leading edge 32 may lie in a single plane, as in FIGS. 13A-13B. The ellipse and/or the single plane may decrease resistance to penetration and/or prevent "peel back" upon insertion of the particular catheter tip. In some embodiments, the single plane may not be normal to the longitudinal axis of the catheter 12 and/or the needle 16. In some embodiments, the tip 96 may correspond to the tip 13, the tip 14, the tip 19, or the tip 92 of the previous Figures.

Figure 14:
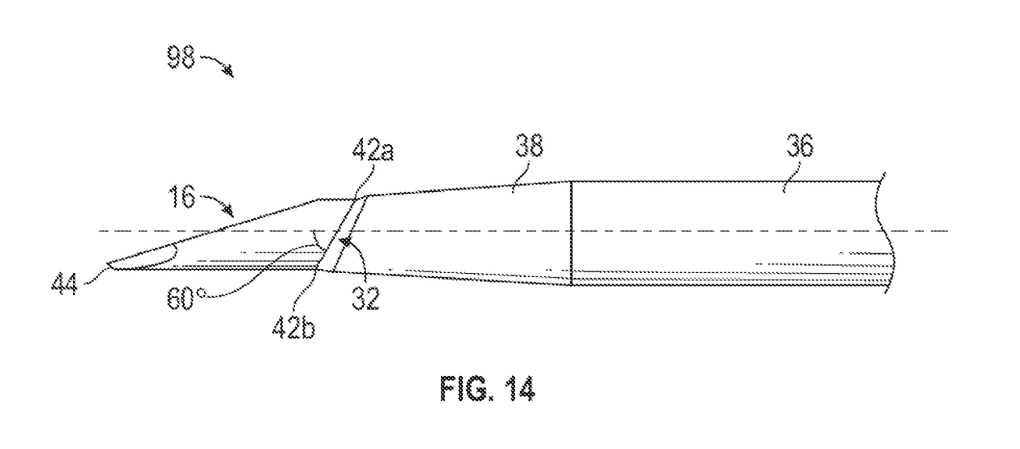
FIG. 14 is a side view of a portion of another example catheter coupled with an example introducer needle, according to some embodiments.

Referring now to FIG. 14, in some embodiments, the leading edge 32 of a catheter tip 98 may be beveled between the upper and lower portions 42a, 42b at an angle of 60 degrees with respect to the longitudinal axis of the catheter 12. In some embodiments, the tip 98 may correspond to the tip 13, the tip 14, the tip 19, or the tip 92 of the previous Figures. In some embodiments, the tip 96 may correspond to the tip 13, the tip 14, the tip 19, the tip 92, or the tip 96 of the previous Figures.

One of skill in the art will appreciate the possible variations and specific features of available vascular access devices, including the PIVC 10 and/or the catheter 12, as are commonly used in the medical and research professions. For example, in some embodiments the PIVC 10 in accordance with the present invention may include additional access sites, clamps, parallel intravenous lines, valves, couplers, introducer needles, coatings, and/or materials as desired to fit a specific application.

Figure 15:
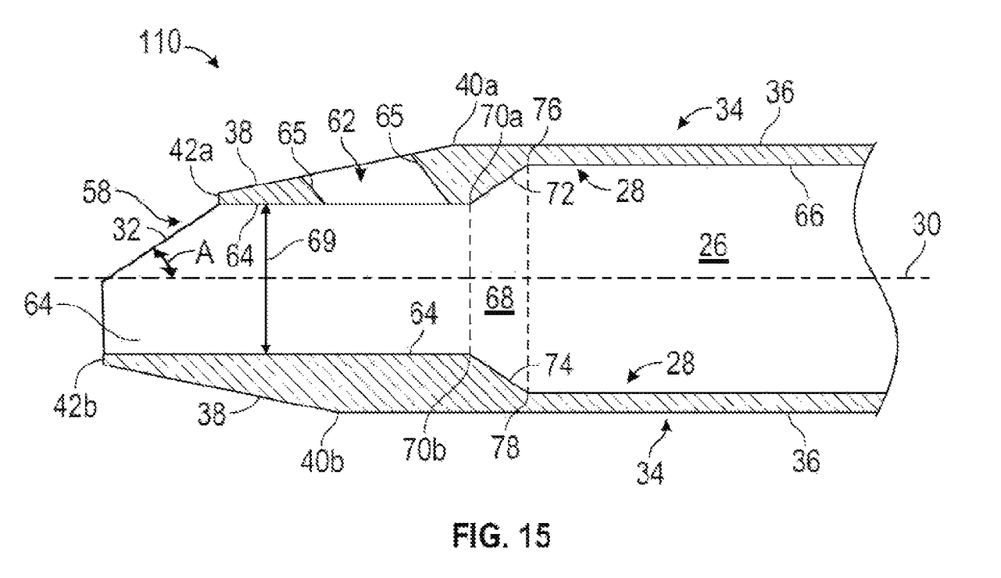
FIG. 15 is a cross-sectional view of a portion of another example catheter, according to some embodiments.

Referring now to FIG. 15, in some embodiments, at least a portion of the leading edge 32 of a catheter tip 110 may be beveled. In some embodiments, a distal portion of the leading edge 32 may be normal with respect to the longitudinal axis 32, while a proximal portion of the leading edge 32 may be beveled at various angles, such as, for example, between 20 and 80 degrees with respect to the longitudinal axis. This angle is shown at "A" on FIG. 15. In some embodiments, the proximal portion of the leading edge 32 may be normal with respect to the longitudinal axis 32, while the distal portion of the leading edge 32 may be beveled at various angles, such as, for example, between 20 and 80 degrees with respect to the longitudinal axis.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter for insertion into a blood vessel, the catheter comprising:
   a catheter body extending between a proximal end configured to be coupled to a catheter adapter and a distal end configured to be inserted into the blood vessel,
   wherein the distal end of the catheter body comprises a distal lumen opening formed by a leading edge, wherein the catheter body comprises a lumen extending from the proximal end of the catheter body to the distal lumen opening,
   wherein the distal end of the catheter body comprises an asymmetric external tapered portion, wherein the asymmetric external tapered portion comprises a first side and a second side opposite the first side, wherein a proximal end of the first side of the asymmetric external tapered portion is offset from a proximal end of the second side of the asymmetric external tapered portion such that the first side and the second side are not diametrically opposed.

2. The catheter of claim 1, wherein the asymmetric external tapered portion comprises a flow hole.

3. The catheter of claim 1, wherein the asymmetric external tapered portion is proximate the leading edge and extends proximally from the leading edge.

4. The catheter of claim 1, wherein the first side of the asymmetric external tapered portion and the second side of the asymmetric external tapered portion are disposed at an angle with respect to a longitudinal axis of the catheter.

5. The catheter of claim 1, wherein the first side of the asymmetric external tapered portion is on a bottom of the catheter body and the second side is on a top of the catheter body, wherein the proximal end of the first side of the asymmetric external tapered portion is distal to the proximal end of the second side of the asymmetric external tapered portion.

6. The catheter of claim 5, wherein the first side of the of the asymmetric external tapered portion comprises a flow hole.

7. The catheter of claim 5, wherein the first side and the second side extend from the leading edge.

* * * * *